(12) United States Patent
Shiramizu et al.

(10) Patent No.: US 10,351,506 B2
(45) Date of Patent: Jul. 16, 2019

(54) PURIFIED PLASTICIZERS, PRODUCTION AND USE

(71) Applicant: ExxonMobil Chemical Patents Inc., Baytown, TX (US)

(72) Inventors: Mika L. Shiramizu, Houston, TX (US); Stephen Zushma, Clinton, NJ (US); Jörg F. W. Weber, Houston, TX (US); Neeraj Sangar, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/072,032

(22) PCT Filed: Apr. 11, 2017

(86) PCT No.: PCT/US2017/026978
§ 371 (c)(1),
(2) Date: Jul. 23, 2018

(87) PCT Pub. No.: WO2017/204913
PCT Pub. Date: Nov. 30, 2017

(65) Prior Publication Data
US 2019/0031593 A1 Jan. 31, 2019

Related U.S. Application Data

(60) Provisional application No. 62/341,988, filed on May 26, 2016.

(30) Foreign Application Priority Data

Jun. 29, 2016 (EP) .................................. 16176778

(51) Int. Cl.
| | | |
|---|---|---|
| C07C 67/54 | (2006.01) | |
| C07C 51/265 | (2006.01) | |
| C07C 67/02 | (2006.01) | |
| C07C 67/03 | (2006.01) | |
| C07C 67/08 | (2006.01) | |
| C07C 63/331 | (2006.01) | |
| C07C 69/76 | (2006.01) | |
| C08K 5/12 | (2006.01) | |

(52) U.S. Cl.
CPC ............ *C07C 67/54* (2013.01); *C07C 51/265* (2013.01); *C07C 67/03* (2013.01); *C07C 67/08* (2013.01); *C07C 63/331* (2013.01); *C07C 69/76* (2013.01); *C08K 5/12* (2013.01)

(58) Field of Classification Search
CPC ......... C07C 67/02; C07C 67/03; C07C 67/08; C07C 67/54; C07C 51/265
See application file for complete search history.

(56) References Cited

U.S. PATENT DOCUMENTS

| | | |
|---|---|---|
| 5,138,022 A | 8/1992 | Mang et al. |
| 9,321,898 B2 | 4/2016 | Dakkat et al. |
| 2010/0159177 A1 | 6/2010 | Dakka et al. |
| 2011/0184105 A1 | 7/2011 | Dakka et al. |
| 2012/0108874 A1 | 5/2012 | Gralla et al. |
| 2014/0212666 A1* | 7/2014 | Dakka ...................... C08K 5/12 428/392 |
| 2014/0315021 A1 | 10/2014 | Naert et al. |
| 2015/0080546 A1* | 3/2015 | Dakka ................... C07C 51/265 528/305 |
| 2015/0361027 A1* | 12/2015 | Dakka ................... C07C 67/035 560/77 |

OTHER PUBLICATIONS

Goodwin, A., "Plasticizers" Applied Polymer Science, pp. 157-175, 2000.

* cited by examiner

*Primary Examiner* — Yate' K Cutliff

(57) ABSTRACT

This disclosure relates to methods for producing purified aromatic esters useful as plasticizers, to the purified aromatic esters, and to polymer compositions containing the purified esters. The purified aromatic esters can be produced by esterifying carboxylic acid with methyl or ethyl alcohol, separating the resulting methyl or ethyl esters from the carboxylic acid and any byproduct impurities, and then transesterifying the methyl or ethyl esters with $C_4$ to $C_{14}$ alcohol to produce the purified aromatic esters. Additionally, precipitation, filtration, and wash steps can be employed to purify the carboxylic acid, the methyl or ethyl alcohol, and/or the aromatic esters.

14 Claims, No Drawings

PURIFIED PLASTICIZERS, PRODUCTION AND USE

CROSS REFERENCE TO RELATED APPLICATIONS

This application is a National Phase Application claiming priority to PCT Application Serial No. PCT/US2017/026978, filed Apr. 11, 2017, which claims priority to and the benefit of U.S. Ser. No. 62/341,988, filed May 26, 2016 and EP 16176778.5, filed Jun. 29, 2016 and are incorporated by reference in their entirety.

FIELD OF THE INVENTION

This disclosure relates to methods for producing purified aromatic esters useful as plasticizers, to the purified aromatic esters, and to polymer compositions containing the purified esters.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Commonly assigned U.S. Pat. No. 9,321,898, incorporated by reference, identified plasticized vinyl chloride formulations using non-phthalate aromatic ester plasticizer. Commonly assigned US 2014-0315021, incorporated by reference, identified various blends of commercially available plasticizers with non-phthalate aromatic ester plasticizers. However, it has been observed that the aromatic esters produced by the methods described in these references contain byproduct impurities, such as aldehydes, acetates and color body impurities, making the esters less desirable for some plasticizer applications.

A method for producing purified aromatic esters is therefore desired.

SUMMARY OF THE INVENTION

The present invention in one aspect relates to a method for producing purified aromatic esters of the following formulas:

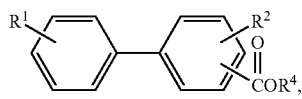

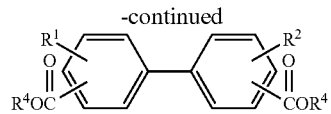

where R1 is a hydrogen or an alkyl, R2 is a hydrogen or an alkyl, and R4 is an alkyl residual of $C_4$ to $C_{14}$ alcohol.

The purified aromatic esters can be produced by esterifying carboxylic acid precursors with methyl or ethyl alcohol, separating the resulting methyl or ethyl esters from the carboxylic acids and any byproduct impurities and then transesterifying the high purity methyl or ethyl esters. Advantageously, the boiling point of the methyl or ethyl esters allows them to be separated from the carboxylic acids and the byproduct impurities at a high purity, e.g., ≥99.0 wt % methyl or ethyl esters. Thus, the invention produces high purity aromatic esters of $C_4$ to $C_{14}$ alcohol, e.g., ≥99.0 wt % aromatic esters of $C_4$ to $C_{14}$ alcohol.

More particularly, the invention is a method for producing purified aromatic esters comprising several steps. First, one or more feed compound(s) are provided of the following Formulas I(a) and/or I(b):

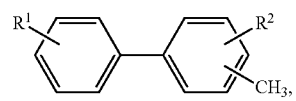

Formula I(a)

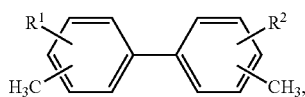

Formula I(b)

where R1 is a hydrogen or an alkyl and R2 is a hydrogen or an alkyl. Second, the feed compound(s) are oxidated to form a first mixture comprising carboxylic acids and byproduct impurities. The carboxylic acids have the following Formulas II(a) and/or II(b):

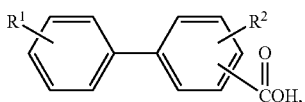

Formula II(a)

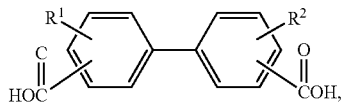

Formula II(b)

where R1 and R2 are as previously defined. The byproduct impurities comprise aldehydes, acetates, and color body impurities formed from under or over-oxidation of the feed compound(s). Third, the carboxylic acids are esterified with methyl or ethyl alcohol (preferably methyl alcohol) to form a second mixture comprising at least a portion of the byproduct impurities and methyl or ethyl esters of the following Formulas III(a) and/or III(b):

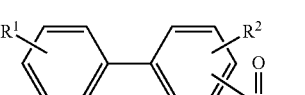

Formula III(a)

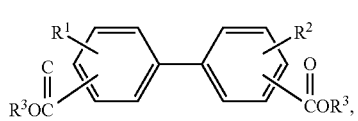

Formula III(a)

where R1 and R2 are as previously defined and R3 is an alkyl residual of the methyl or ethyl alcohol. Fourth, the methyl or ethyl esters are separated from substantially all the byproduct impurities in the second mixture to form purified methyl or ethyl esters. Fifth, the purified methyl or ethyl esters are transesterified with $C_4$ to $C_{14}$ alcohol to form a third mixture comprising methyl or ethyl alcohol and aromatic esters of the following Formulas IV(a) and IV(b):

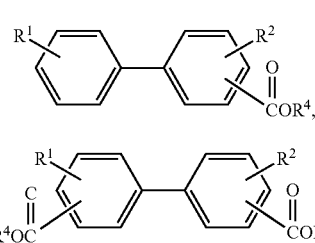

Formula IV(a)

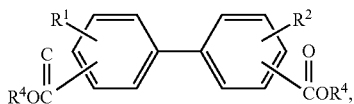

Formula IV(b)

where R1 and R2 are as previously defined and R4 is an alkyl residual of $C_4$ to $C_{14}$ alcohol. Sixth, the aromatic esters are separated from the methyl or ethyl alcohol in the third mixture to form the purified aromatic esters. In a preferred embodiment of the invention, the purified aromatic esters comprise methylbiphenyl carboxylic acid esters of $C_4$ to $C_{14}$ alcohol.

In any aspect of the invention, optionally, the first mixture is cooled to form a precipitate, the precipitate is filtered and washed with water and/or solvent to remove at least a portion of byproduct impurities prior to esterifying the carboxylic acid with methyl or ethyl alcohol.

DETAILED DESCRIPTION OF THE INVENTION

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

A method has been determined for producing purified aromatic esters of the above Formulas IV(a) and IV(b), where R1 is a hydrogen or an alkyl, R2 is a hydrogen or an alkyl, and R4 is an alkyl residual of $C_4$ to $C_{14}$ alcohol. An important aspect of the invention is the derivation of carboxylic acids to methyl or ethyl esters and the separation of those methyl or ethyl esters, e.g., by distillation, from various byproduct impurities.

Carboxylic acids can be produced by the aerobic partial oxidation of one or more feed compound(s) having the above Formulas I(a) and I(b) (reproduced here for convenient reference):

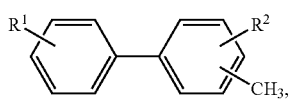

Formula I(a)

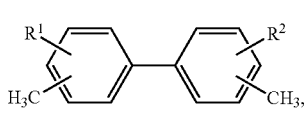

Formula I(b)

where R1 is a hydrogen or an alkyl and R2 is also a hydrogen or an alkyl. In any embodiment, the feed compounds comprise biphenyl substituted with at least one methyl group. Optionally, the feed compounds comprise biphenyl substituted with one methyl group and one or more additional alkyl groups. Preferably, the feed compounds comprise one or more isomers of dimethylbiphenyl.

The oxidation of the feed compound produces desired carboxylic acids of the above Formulas II(a) and II(b) (reproduced here for convenient reference):

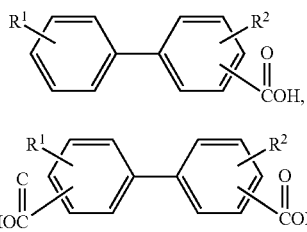

Formula II(a)

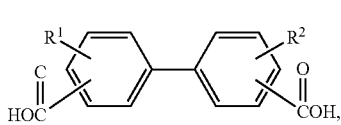

Formula II(b)

where R1 and R2 are as previously defined. Preferable carboxylic acids are one or more isomers of methylbiphenylcarboxylic acid and/or biphenyldicarboxylic acid.

The oxidation is accompanied by various undesired byproduct impurities in the form of under and over-oxidated species as well as trace color body impurities such as fluorine, fluorenone, alkyl-substituted flourene, and alkyl-substituted fluorenone. Some examples of under-oxidated species include monoalcohols, monoacetates and monoaldehydes of the following formulas respectively:

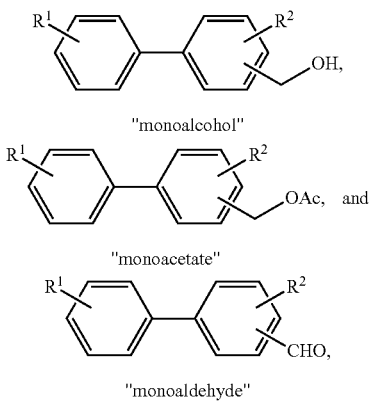

where R1 and R2 are as previously defined (R1 is a hydrogen or an alkyl and R2 is a hydrogen or an alkyl).

In embodiments where only carboxylic mono-acid is desired, over oxidation results in carboxylic acids of Formula II(a) described above except that alkyl R1 and/or R2 is oxidated to form an acetate, aldehyde or another carboxylic acid (i.e., an acetate-acid, aldehyde-acid, or di-acid was formed). Some examples of species resulting from over-oxidation of dimethylbiphenyl are acetooxymethylbiphenylcarboxylic acid, formylbiphenylcarboxylic acid, and biphenyldicarboxylic acid (when only mono-acid is desired) with the following formulas respectively:

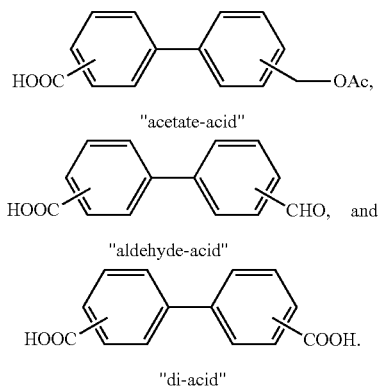

"acetate-acid"

"aldehyde-acid"

"di-acid"

In an embodiment, the feed compounds are oxidized to form a first mixture comprising carboxylic acids and byproduct impurities, the carboxylic acids having the above Formula II(a) and II(b), where R1 is a hydrogen or an alkyl and R2 is a hydrogen or an alkyl, the byproduct impurities comprising aldehydes, acetates, and color body impurities formed from under or over-oxidation of the feed compounds.

Co-pending US 2014/0212666 (see e.g., Experiments 30F and 30G), incorporated by reference, describe oxidation methods suitable for the feed compounds described herein.

Oxidation of the feed compounds can be performed by any process known in the art, such as by reacting the feed compounds with an oxidant, such as oxygen, ozone or air, or any other oxygen source, such as a peroxide (i.e., hydrogen peroxide), in the absence or presence of a catalyst, with or without a promoter. The oxidation can be performed at temperatures from 30° C. to 300° C., such as from 50° C. to 200° C., alternately from 60° C. to 180° C., alternately from 90° C. to 160° C.

Promoters comprising a Br compound are preferably absent. If promoters comprising Br compounds are present, the promoters present a weight ratio of catalyst metal to bromine of less than 100:1, alternately at less than 1000:1. Preferably, if present, the promotors comprising Br compound are present in an amount having a negligible effect on the oxidation reaction.

The oxidation is preferably performed in the presence of a solvent. Useful solvents for the oxidation include acetic acid.

The oxidation may be conducted in the absence or presence of a catalyst. Suitable catalysts comprise Co or Mn or a combination of both metals. Useful oxidation catalysts include cobalt acetate, cobalt (II) chloride hexahydrate.

Additional suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N,N'-dihydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-trihydroxyisocyanuric acid. These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %.

Another aspect of the invention relates to several precipitation, filtration, solvent and/or water washing steps optionally added to remove at least a portion of byproduct impurities prior to esterifying carboxylic acid with methyl or ethyl alcohol.

Following oxidation, the first mixture additionally comprises solvent, optionally catalyst and/or promoter, and unreacted feed compound(s). The first mixture can be cooled to precipitate carboxylic acid. Anti-solvent, such as but not limited to water, can optionally be added to increase precipitation of carboxylic acid. The first mixture precipitate is filtered to recover the precipitate from a majority of the reaction solvent and catalyst. The recovered first mixture precipitate can be washed with organic wash solvent (e.g., hexane) or a mixed wash solvent (e.g., acetic acid-water mixture) to remove at least a portion of more soluble byproduct impurities such as unreacted feed compounds and under-oxidated species, e.g., monoalcohol, monoaldehyde, and monoacetate. The cooled, filtered and washed first mixture precipitate comprises primarily carboxylic acid and over-oxidated species as well as residual under-oxidated species and trace color body impurities.

In an embodiment, the first mixture is cooled to form a first mixture precipitate, the first mixture precipitate is filtered and washed with water and/or solvent to remove at least a portion of byproduct impurities prior to esterifying the carboxylic acid with methyl or ethyl alcohol.

Separation of the byproduct impurities to purify the carboxylic acid before esterification has proven difficult. Particularly difficult is removal of the color body impurities whose presence in even trace amounts can affect product quality of aromatic esters formed in their presence. Similarly, separation of the byproduct impurities after esterification of the carboxylic acid mixture directly to the desired aromatic esters of $C_4$ to $C_{14}$ alcohols has also proven difficult. Either separation approach on its own or both separation approaches together have resulted in observed color impurities and degraded performance qualities making the aromatic esters less desirable for applications such as a plasticizer or as a PVC plastisol component.

To address this issue, at least a portion of carboxylic acids in the first mixture are esterified with either methyl or ethyl alcohol to form a second mixture comprising at least a portion of the byproduct impurities and methyl or ethyl esters of the above Formulas III(a) and/or II(b), where R1 is a hydrogen or an alkyl, R2 is a hydrogen or alkyl, and R3 is an alkyl residual of the methyl or ethyl alcohol. Preferably the carboxylic acids are esterified with methyl alcohol.

Some of the byproduct impurities, particularly the over-oxidated species, present in the first mixture are also esterified to produce, for example, acetate-esters and aldehyde-esters of the methyl or ethyl alcohol. For clarity, the byproduct impurities of the second mixture (i.e., second mixture byproduct impurities) include esterified species as well as some species that do not participate in the esterification reactions or that remain unreacted. Conversely, the byproduct impurities of the first mixture (i.e., first mixture byproduct impurities) do not include esterified species.

It has been discovered that the methyl or ethyl esters in the second mixture have a volatility that allows separation using commercially desirable amounts of heat and/or vacuum. The volatility of the methyl or ethyl esters is sufficiently different from the byproduct impurities to allow separation of the methyl or ethyl esters to a high purity. In an embodiment, the methyl or ethyl esters are separated to a purity of ≥99.0 wt % methyl or ethyl esters. In an embodiment, the methyl or ethyl esters are separated from substantially all the byproduct impurities in the second mixture to form purified methyl or ethyl esters.

The separation of methyl or ethyl esters can be by any known separation method utilizing relative volatility as the separation mechanism. The separation can be performed in one or more separation stages. In non-limiting embodiments, the separation of methyl or ethyl esters is by evaporative separation, flash separation, distillation, packed column, and/or vacuum distillation. In a preferred embodiment, the separation of methyl or ethyl esters is by vacuum distillation.

"Esterifying" or "esterification" is a reaction of a carboxylic acid moiety with an organic alcohol moiety to form an ester and water. Esterification conditions are well-known in the art and include, but are not limited to, temperatures of 0-300° C., and the presence of homogeneous or heterogeneous esterification catalysts such as Lewis or Brnsted acid catalysts. The following equation depicts the esterification equilibrium reaction for the compounds described herein:

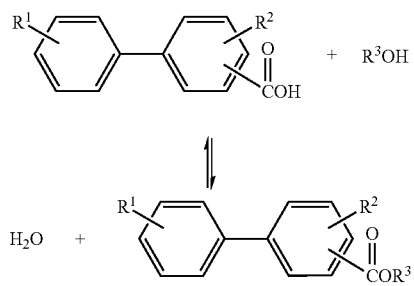

where R1 and R2 are as previously defined. R3 is the methyl or ethyl alkyl group of the methyl or ethyl alcohol and the methyl or ethyl esters.

In an embodiment, the carboxylic acids are esterified with methyl or ethyl alcohol at a temperature from 0-300° C. in the presence of homogeneous or heterogeneous esterification catalyst, the esterification catalyst comprising Lewis or Brönsted acid catalysts to form a second mixture comprising at least a portion of the byproduct impurities and methyl or ethyl esters.

Following esterification, the second mixture additionally comprises water and, catalyst. Optionally, the second mixture can be cooled to form a second mixture precipitate. The second mixture precipitate can be filtered to recover the precipitate from a majority of the water and catalyst. The recovered second mixture precipitate can be washed with water to further remove catalyst and subsequently dried to remove water. The cooled, filtered, washed, and dried second mixture precipitate comprises primarily methyl or ethyl esters, carboxylic acid and byproduct impurities. The methyl or ethyl esters can be separated as described above from substantially all the unreacted carboxylic acid and byproduct impurities as described above based on difference in relative volatility.

In an embodiment, the second mixture is cooled to form a second mixture precipitate, the second mixture precipitate is filtered, washed with water to remove any acid catalyst, and dried to remove water prior to separating the methyl or ethyl esters from substantially all byproduct impurities to form purified methyl or ethyl esters.

Purified Aromatic Esters of $C_4$ to $C_{14}$ Alcohol

In one aspect of the invention, purified aromatic esters of $C_4$ to $C_{14}$ alcohol are desired. The purified methyl or ethyl esters are subsequently transesterified with $C_4$ to $C_{14}$ alcohol to form a third mixture comprising methyl or ethyl alcohol and aromatic esters of the above Formulas IV(a) and/or IV(b) (reproduced here for convenient reference)

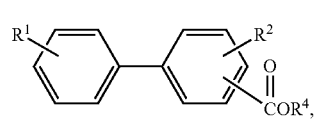

Formula IV(a)

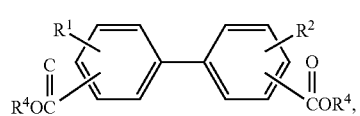

Formula IV(b)

where R1 is a hydrogen or an alkyl, R2 is a hydrogen or an alkyl, and R4 is an alkyl residual of $C_4$ to $C_{14}$ alcohol.

The aromatic esters are subsequently separated from the methyl or ethyl alcohol in the third mixture, e.g., by distillation, to form a purified aromatic ester product. In an embodiment, the purified aromatic ester product comprises ≥99.0 wt % aromatic ester based on the weight of the purified aromatic ester product.

In a preferred embodiment, the purified aromatic esters are methylbiphenylcarboxylic acid esters of $C_4$ to $C_{14}$ alcohols.

In an embodiment, the purified aromatic ester product comprises ≥99.0 wt % methylbiphenylcarboxylic acid esters of $C_4$ to $C_{14}$ alcohol based on the weight of the purified aromatic ester product.

In still another embodiment, a method for producing purified aromatic esters comprises several steps. First, feed comprising dimethylbiphenyl is provided. Second, the feed is oxidated to form a first mixture comprising methylbiphenylcarboxylic acid and byproduct impurities, the byproduct impurities comprising biphenyldicarboxylic acid, methylbiphenyl carbaldehyde, methylbiphenylmethylacetate, and/or methylfluorenone. Third, the methylbiphenylcarboxylic acid is esterified with methyl or ethyl alcohol to form a second mixture comprising at least a portion of the byproduct impurities and methyl or ethyl esters of methylbiphenylcarboxylic acid. Fourth, the methyl or ethyl esters are separated from substantially all the byproduct impurities in the second mixture to form purified methyl or ethyl esters. Fifth, the purified methyl or ethyl esters are transesterified with $C_4$ to $C_{14}$ alcohol to form a third mixture comprising methyl or ethyl alcohol and methylbiphenylcarboxylic acid esters of the following Formula V:

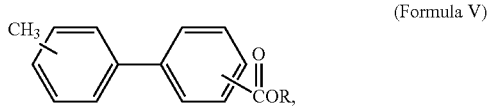

(Formula V)

where R is an alkyl residual of $C_4$ to $C_{14}$ alcohol. Sixth, the methylbiphenyl carboxylic acid esters of $C_4$ to $C_{14}$ alcohol are separated from the methyl or ethyl alcohol in the third mixture to form the purified aromatic esters.

"Transesterifying" or "transesterification" is an equilibrium reaction where the alkyl group R3 of an ester is exchanged with the alkyl group R4 of an alcohol. The following equation depicts the transesterification equilibrium reaction for the compounds described herein:

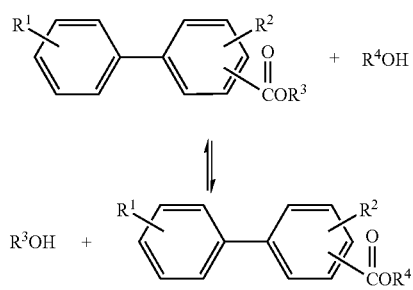

where R1 and R2 are as previously defined. R3 is the methyl or ethyl alkyl group of the methyl or ethyl esters, and R4 is the alkyl group of the $C_4$ to $C_{14}$ transesterification alcohols. Esters with $C_4$-$C_{14}$ alkyl groups can be produced in high purity from esters of methyl or ethyl alcohol by shifting equilibrium in favor of the $C_4$-$C_{14}$ alkyl group esters by i) heating a reaction mixture of methyl or ethyl ester and $C_4$-$C_{14}$ alcohol to evaporate the lower boiling methyl or ethyl alcohol as it is formed and/or ii) adding excess $C_4$-$C_{14}$ alcohol. The transesterification can be in the presence of an acid or base catalyst. Preferably the transesterification is in the presence of an acid catalyst.

Transterification conditions are well-known in the art and include, but are not limited to, temperatures of 0-300° C., and the presence of homogeneous or heterogeneous esterification catalysts such as Lewis or Brnsted acid catalysts.

In an embodiment, the purified methyl or ethyl esters are transesterified with $C_4$ to $C_{14}$ alcohol at a temperature from 0-300° C. in the presence of homogeneous or heterogeneous esterification catalyst, the esterification catalyst comprising Lewis or Brnsted acid catalysts to form a third mixture comprising methyl or ethyl alcohols and aromatic esters of $C_4$ to $C_{14}$ alcohol.

In a preferred embodiment of the invention, after transesterifying with $C_4$ to $C_{14}$ alcohol under transesterification conditions, the aromatic esters are contacted with a basic solution such as saturated sodium carbonate or a caustic soda wash to quench or stop the reaction.

In a preferred embodiment of the invention, the aromatic ester is further stripped to remove excess alcohol and the stripped aromatic ester is optionally treated with activated carbon or clay to improve product quality and color of the aromatic ester.

Any known $C_4$ to $C_{14}$ alcohols can be used to transesterify the purified methyl or ethyl esters. The purified methyl or ethyl esters can be transesterified with one or more $C_4$ to $C_{14}$ alcohols. In a preferred embodiment, the purified methyl or ethyl esters are tranesterified with $C_4$ to $C_{14}$ OXO-alcohols, the formation of which is described in more detail below.

"OXO-alcohols" are isomeric linear, branched, or mixtures of linear and branched, organic alcohols. "OXO-esters" are compounds having at least one functional ester moiety within its structure derived from esterification of a carboxylic acid portion or moiety of a compound with an OXO-alcohol.

OXO-alcohols can be prepared by hydroformylating olefins, followed by hydrogenation to form the alcohols. "Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogeneous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, incorporated herein by reference in its entirety. Olefins for hydroformylation can also be prepared by dimerization of propylene or butenes through commercial processes such as the IFP Dimersol™ process or the Huls (Evonik) Octol™ process.

Branched aldehydes are then produced by hydroformylation of the isomeric olefins. The resulting branched aldehydes can then be recovered from the crude hydroformylation product stream by fractionation to remove unreacted olefins. These branched aldehydes can then be hydrogenated to form alcohols (OXO-alcohols). Single carbon number alcohols can be used in the esterification of the acids described above, or differing carbon numbers can be used to optimize product cost and performance requirements. The "OXO" technology provides cost advantaged alcohols. Other options are considered, such as hydroformylation of $C_4$-olefins to $C_5$-aldehydes, followed by hydrogenation to $C_5$-alcohols, or aldehyde dimerization followed by hydrogenation to $C_{10}$ alcohols.

"Hydrogenating" or "hydrogenation" is addition of hydrogen ($H_2$) to a double-bonded functional site of a molecule, such as in the present case the addition of hydrogen to the aldehyde moieties of a di-aldehyde, to form the corresponding di-alcohol, and saturation of the double bonds in an aromatic ring. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as, but not limited to Pt/C, Pt/$Al_2O_3$ or Pd/$Al_2O_3$ and Ni. Useful hydrogenation catalysts include platinum, palladium, ruthenium, nickel, zinc, tin, cobalt, or a combination of these metals, with palladium being particularly advantageous.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

The $C_4$ to $C_{14}$ alcohols can be used individually or together in alcohol mixtures having different chain lengths, or in isomeric mixtures of the same carbon chain length to transesterify the purified methyl or ethyl esters and make aromatic esters of mixed alcohols for use as plasticizers. This mixing of carbon numbers and/or levels of branching in the can be advantageous to achieve the desired compatibility with PVC and to meet other plasticizer performance properties. The preferred alcohols for transesterification are those having from 5 to 13 carbons, more preferably $C_5$ to $C_{11}$ alcohols, and even more preferably $C_6$ to $C_{10}$ alcohols.

In one embodiment, the preferred alcohols for transesterification are those which have an average branching of from 0.2 to 5.0 branches per molecule, and from 0.35 to 5.0 methyl branches per molecule, or even from 1.3 to 5.0 methyl branches per molecule. In a more preferred embodiment, the alcohols have from 0.05 to 0.4 branches per residue at the alcoholic beta carbon.

As a non-limiting example of suitable branched alcohols, the branching characteristics of OXO-alcohols are provided in Table 1, below.

TABLE 1

$^{13}$C NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4^e$ | 4.0 | 0 | 0.35 | 1.35 | 0.35 | 0 |
| $C_5^f$ | 5.0 | 0 | 0.30 | 1.35 | 0.35 | 0 |
| $C_6$ | — | — | — | — | — | — |
| $C_7$ | 7.2 | 0 | 0.13 | 2.2 | — | 0.04 |
| $C_8$ | 8.0 | 0 | 0.08 | 2.6 | — | — |
| $C_9$ | 9.3 | 0 | 0.09 | 3.1 | — | — |
| $C_{10}$ | 10.1 | 0 | 0.08 | 3.1 | — | — |
| $C_{12}$ | 11.8 | 0 | 0.09 | 3.9 | — | — |
| $C_{13}$ | 12.7 | 0 | 0.09 | 3.9 | — | — |

—Data not available.
[a]—COH carbon.
[b]Branches at the—CCH$_2$OH carbon.
[c]This value counts all methyl groups, including C$_1$ branches, chain end methyls, and methyl endgroups on C$_2$+ branches.
[d]C$_1$ branches only.
[e]Calculated values based on an assumed molar isomeric distribution of 65% n-butanol and 35% isobutanol (2-methylpentanol).
[f]Calculated values based on an assumed molar isomeric distribution of 65% n-pentanol, 30% 2-methylbutanol, and 5% 3-methylbutanol.

In a preferred embodiment of the invention, the transesterification alcohol (such as an OXO-alcohol) has 2.0 to 3.5 methyl branches per molecule, typically 2.1 to 3.3.

In general, for every polymer to be plasticized, a plasticizer is required with a good balance of polarity or solubility, volatility and viscosity to have acceptable plasticizer compatibility with the resin. In particular, if the 20° C. kinematic viscosity is higher than 250 mm$^2$/sec as measured by the appropriate ASTM test, or alternately if the 20° C. cone-and-plate viscosity is higher than 250 cP, this will affect the plasticizer processability during formulation, and can require heating the plasticizer to ensure good transfer during storage and mixing of the polymer and the plasticizer. Volatility is also an important factor which affects the ageing or durability of the plasticized polymer. Highly volatile plasticizers will diffuse and evaporate from the plastic resin matrix, thus losing mechanical strength in applications requiring long term stability/flexibility. Relative plasticizer loss from a resin matrix due to plasticizer volatility can be roughly predicted by neat plasticizer weight loss at 220° C. using Thermogravimetric Analysis.

We have found that when $C_4$ to $C_{14}$ alcohols are used as reactants for the transesterification reactions described above, the resulting aromatic esters are in the form of relatively high-boiling liquids (having low volatility), which are readily incorporated into polymer formulations as plasticizers.

Any of the aromatic esters having alkyl residues of $C_4$ to $C_{14}$ alcohols, can be used as plasticizers for polymers, such as vinyl chloride resins, polyesters, polyurethanes, silylated polymers, polysulfides, acrylics, ethylene-vinyl acetate copolymer, rubbers, poly(meth)acrylics and combinations thereof, preferably polyvinylchloride.

EXAMPLES

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure can be practiced otherwise than as specifically described herein.

Example 1

Oxidation

Feed compounds comprising a mixture of dimethylbiphenyl (DMBP) isomers (3,3'-dimethylbiphenyl, 3,4'-dimethylbiphenyl, and 4,4'-dimethylbiphenyl) were combined with acetic acid (AcOH) in proportions 20 parts DMBP / 80 parts AcOH by weight. The feed compound—acetic acid mixture was divided into several 1 kg batches. Oxidation of each batch was performed at 150° C. for 1 h with 1500 ppm cobalt acetate catalyst and air (21% oxygen) at 500 psig. Table 2 below summarizes a typical organic composition observed for the crude oxidation product (first mixture). Note each concentration listed is a sum of all isomers.

TABLE 2

| Organic Composition | wt % |
|---|---|
| All unknowns | 3.5 |
| Dimethylbiphenyl (DMBP) | 20.8 |

TABLE 2-continued

| Organic Composition | wt % |
|---|---|
| Methylbiphenylcarbaldehyde (monoaldehyde) | 9.4 |
| Methylbiphenylmethanol (monoalcohol) | 0.6 |
| Methylbiphenylmethylacetate (monoacetate) | 2.1 |
| Methylbiphenylcarboxylic acid (monoacid) | 53.6 |
| Formylbiphenylcarboxylic acid (aldehyde-acid) | 3.8 |
| Acetoxymethylbiphenylcarboxylic acid (acetate-acid) | 1.2 |
| Biphenyldicarboxylic acid (diacid) | 5.1 |

Unreacted DMBP and undesired byproducts, such as under and over-oxidated species are present in the oxidation product.

Example 2

Precipitation/Filtration

A crude oxidation product (first mixture) prepared according to Example 1 was cooled to room temperature and formed a suspension (solid precipitate+liquid). A 1 L sample of the suspension (crude oxidation product in AcOH) was mixed well and then poured into 2 L of water in a 4 L wide-mouth bottle resulting in further precipitate formation. The 4 L bottle was closed and shaken well. The contents of the 4 L bottle were filtered to recover the solid precipitate.

Example 3

Water Wash

A filtered solid precipitate prepared according to Example 2 was placed in another 4 L wide-mouth bottles along with 2 L of fresh water. The resulting suspension was shaken to mix and then filtered to recover one time water-washed precipitate. The water wash was repeated one to two more times to recover an up to three times water-washed precipitate.

Example 4a

Hexanes Wash

A water-washed, wet precipitate prepared according to Example 3, usually about 300-350 g (wet weight), was placed in a 4 L wide-mouth bottle with 1 L of hexanes. The mixture was shaken and filtered to recover a white solid precipitate. The hexane wash was repeated one to two more times to recover an up to three times hexane-washed solid precipitate. The precipitate was dried overnight in vacuum oven at 75° C. Typical washed and dried (first mixture) precipitate weight observed following procedures in Examples 1-4 was about 112 g per batch. Table 3a contains gas chromatograph (GC) composition analysis of the Example 2, 3, and 4a precipitate filter cakes as well as the methylbiphenylcarboxylic acid (monoacid) isomer distribution for each of the precipitate filter cakes.

TABLE 3a

| Compound | Example 2 Precipitate wt % (crude oxidation product) | Example 3 Precipitate wt % (3x water-washed) | Example 4a Precipitate wt % (1x hexanes-washed) | Example 4a Precipitate wt % (2x hexanes-washed) | Example 4a Precipitate wt % (3x hexanes-washed) |
|---|---|---|---|---|---|
| methylbenzoate | 1.47 | 0.82 | 0.62 | 0.53 | 0.38 |
| methyl biphenyl | 0.16 | 0.22 | 0.00 | 0.00 | 0.00 |
| DMBP | 27.17 | 25.46 | 10.21 | 3.07 | 1.13 |
| terephthalic acid | 0.22 | 0.23 | 0.32 | 0.40 | 0.37 |
| monoaldehyde | 9.24 | 7.87 | 4.61 | 2.16 | 1.50 |
| monoalcohol | 1.16 | 1.13 | 0.74 | 0.29 | 0.25 |
| monoacetate | 1.26 | 1.34 | 0.53 | 0.21 | 0.00 |
| Monoacid | 51.56 | 55.17 | 71.38 | 79.89 | 82.06 |
| aldehyde-acid | 2.64 | 2.89 | 4.08 | 4.64 | 4.82 |
| diacid | 3.31 | 3.33 | 6.26 | 7.79 | 8.42 |
| acetate-acid | 0.35 | 0.38 | 0.66 | 0.60 | 0.62 |
| Unknowns | 1.47 | 1.16 | 0.59 | 0.44 | 0.45 |
| Monoacid Isomer Distribution (wt %) | | | | | |
| 3-methylbiphenyl-3-carboxylic acid | 12.29 | 12.31 | 8.45 | 6.86 | 6.17 |
| 4-methylbiphenyl-3-carboxylic acid | 6.00 | 5.83 | 5.02 | 4.83 | 4.70 |
| 3-methylbiphenyl-4-carboxylic acid | 58.06 | 59.03 | 62.41 | 63.72 | 64.11 |
| 4-methylbiphenyl-4-carboxylic acid | 23.65 | 22.84 | 24.13 | 24.58 | 25.02 |

Approximately 90% of monoacid in the crude oxidation product precipitate was recovered after water and hexane washing.

Example 4b

Acetic Acid/Water Mixture Wash

A water-washed, wet precipitate prepared according to Examples 1-3, was placed in a wide-mouth bottle with a 9:1 ratio acetic acid:water wash solution. The mixture was shaken and filtered to recover a white solid precipitate. The acetic acid/water wash was repeated one to two more times to recover an up to three times acetic acid/water washed solid precipitate. The precipitate was dried overnight in vacuum oven at 75° C. Table 3b contains gas chromatograph (GC) composition analysis of the filtered crude oxidation product prepared according to Example 2 and the Example 4b precipitate filter cakes.

TABLE 3b

| Compound | Example 2 Precipitate wt % (crude oxidation product) | Example 4b Precipitate wt % (3x acetic acid/water washed) |
|---|---|---|
| DMBP | 20.5 | 0.1 |
| monoaldehyde | 9.3 | 0.8 |
| monoalcohol | 0.5 | 0.1 |
| monoacetate | 2.1 | 0.0 |
| Monoacid | 54.5 | 79.7 |
| aldehyde-acid | 3.9 | 5.1 |
| diacid | 4.4 | 13.2 |
| acetate-acid | 1.2 | 0.5 |
| Unknowns | 3.5 | 0.5 |

Example 5

Esterification with Methyl Alcohol

A 1 L solution of 2.5 vol % $H_2SO_4$ in methanol (MeOH) was prepared. A 40 g amount of the 3× water and 3× hexanes-washed filtrate (containing approximately 33 g methylbiphenylcarboxylic monoacid) was charged to a 1 L 3-neck flask equipped with a magnetic stirbar, a reflux condenser, a thermocouple and a N2 line. An amount of 320 mL of 2.5% $H_2SO_4$/MeOH solution was added to the flask. A slow nitrogen ($N_2$) stream flow was introduced to purge overhead space. Heat was added to bring the 3-neck flask contents to reflux (65° C.) esterification temperature. Once reflux was achieved, the nitrogen flow was stopped.

Reflux and esterification was continued for approximately 7.5 hours. The conversion of methylbiphenylcarboxylic acid was monitored via GC analysis of periodic samples until it reached >95%. The flask contents stayed as suspension, not a clear homogeneous solution. The term "conversion" as used in this context refers to monoacid conversion. The conversions of other acids such as diacid, aldehyde-acid, and acetate-acid are not considered for purposes of measuring esterification progress. The isomers are totaled for purposes of the conversion calculation, although the rate of methyl esterification reaction of monoacid appeared virtually the same between isomers (i.e., the original monoacid isomer distribution among 3,3',3,4',4,3',4,4' isomers are similar to corresponding methyl ester isomer distribution among 3,3', 3,4',4,3',4,4' isomers over different conversion samples.)

The final conversion was 97%. After final conversion is reached, heat was removed and the esterification product (i.e., the second mixture or the final conversion contents of the flask) was cooled to room temperature. The flask was chilled in a fridge at 7° C. overnight to form a solid precipitate.

The precipitated solid was recovered by filtration. Acidic filtrate was yellow. The filter cake was washed with water five times by putting filtrate in a jar, adding about 50 mL water, shaking, and filtering to remove residual $H_2SO_4$. The pH of the filtrate increased from 0 to 5-6 when measured by pH paper. The washed filtrate was a white powder.

The recovered powder was transferred to a distillation pot flask (pre-weighed), and dried in vacuum oven at about 75° C. with house vacuum and a low flow of purge nitrogen ($N_2$) overnight to remove the residual water. An amount of 26.8 g of dry washed filtrate material was obtained. The filtrate contained 24.4 g of methylbiphenylmethylcarboxylic acid ester (methyl ester) measured by GC analysis. This represents about a 70% yield from 33g of monoacid (24.4/33=72.7%).

Example 6

Distillation (Separation) of Methyl Ester

Distillation was done in a 15 stage spinning band distillation apparatus (B/R Instrument, 800 micro spinning band distillation unit). A charge of washed and dried filtrate prepared according to Example 5 introduced to the distillation apparatus. Distillation conditions included a vacuum of 1.3 to 1 8 mmHg, a head temperature of 140-150° C., a pot temperature of 170-206° C., and a reflux ratio of 30:1 to 10:1. Cuts were collected every 2-3 g. The charged starting feed (methyl esters) was 50 to 75 g.

The middle cuts were combined to form a purified methyl ester.

Example 7

Transesterification (120° C.)

A charge of 3 g (13.3 mmol) of purified methyl ester produced according to Examples 1-6 was added to a 20 mL vial with a screw-top cap and septum. Exxal 10™ alcohol, a commercially available Cio containing alcohol from ExxonMobil, was added under nitrogen in an amount of 5.25 g (6.25 mL, 33.2 mmol or 2.5 times as many mols of methyl ester) with a magnetic stirbar.

Inlet and outlet needles were inserted into the septum. The inlet needle was connected to a Schlenk line, and a low bubble flow of nitrogen ($N_2$) was introduced. The temperature of the vial contents was raised to 80° C. with magnetic stirring. The methyl esters dissolved at this temperature. $N_2$ bubbling continued at 80° C. for 2-3 hours to degas.

After degassing, the temperature of vial contents was increased to 120° C. TIOT catalyst (Titanium(IV) 2-ethylhexyloxide, CAS 1070-10-6) was added via syringe in an amount of 32 uL (30.0 mg, 0.0532 mmol, 0.4 mol %. The transesterification reaction was allowed to progress while maintaining the vial contents at 120° C. with continued N2 flow and magnetic stirring. The transesterification reaction progress was monitored by GC analysis of periodic samples (i.e., the disappearance of Methyl ester and the appearance of Cio ester was monitored).

When conversion to $C_{10}$ ester reached >99 mol % as measured by GC, the temperature was decreased to 90° C. An amount of 0.1 mL of 5% $Na_2CO_3$ aq. solution was added and stirring was continued at 90° C. for 0.5-1 hour to quench. Subsequently, a small amount (3-5 mg) of charcoal and celite were added and stirring was continued at 90° C. for additional 0.5-1 hour.

Nitrogen purge and magnetic stirring were stopped. The vial contents (i.e., the third mixture) were filtered. Methyl alcohol and excess $C_{10}$ alcohol were removed by Kugelrohr distillation or rotaevap at 120° C. and <1 mmHg pressure to yield purified aromatic esters of Exxal 10™ alcohols (i.e., $C_{10}$ alcohols).

Example 8

Transesterification (190° C.)

In a separate experiment from Example 7, a charge of 10 g (44.25 mmol) of purified methyl ester produced according to Examples 1-6 was added to a 100 mL roundbottom 2-neck flask with a septum cap. The flask and contents were purged with $N_2$ by cycling between adding N 2 and evacuating for 3-4 cycles.

Exxal 10™ alcohol, a commercially available Cm containing alcohol from ExxonMobil, was added to the flask under nitrogen in an amount of 20.8 mL (17.5g, 110.6 mmol or 2.5 times as many mols of methyl ester) with a magnetic stirbar. A low bubble flow of nitrogen ($N_2$) was introduced. The temperature of the vial contents was raised to 80° C. with magnetic stirring. $N_2$ bubbling continued at 80° C. for 2-3 hours to degas.

After degassing, the temperature of flask contents was increased to 160° C. TIOT catalyst (Titanium(IV) 2-ethylhexyloxide, CAS 1070-10-6) was added via syringe in an amount of 0.11 mL (100 mg, 0.177 mmol, 0.4 mol %).

After addition of TIOT catalyst, the temperature of the flask contents was increased to 190° C. Transesterification was allowed to progress at this temperature with continued $N_2$ flow and magnetic stirring. The transesterification reaction progress was monitored by GC analysis of periodic samples (i.e., the disappearance of Methyl ester and the appearance of $C_{10}$ ester was monitored).

When conversion to $C_{10}$ ester reached >99 mol % as measured by GC (1 to 2 hours), the temperature was decreased to 90° C. An amount of 0.56 mL of 5% $Na_2CO_3$ aq. solution (contains 0.028 g of $Na_2CO_3$ or 1.5 equivalents $Na_2CO_3$ to TIOT) was added and stirring was continued at 90° C. for 0.5-1 hour to quench. Subsequently, a small amount (about 25 mg) of charcoal was added and stirring was continued at 90° C. for additional 0.5-1 hour.

Nitrogen flow and magnetic stirring were stopped. The flask contents (i.e., the third mixture) was filtered through a celite layer (about 50 mg) into another round bottom flask. Methyl alcohol and excess $C_{10}$ alcohol were removed by Kugelrohr distillation or rotaevap at 120° C. and <1 mmHg pressure to yield purified aromatic esters of Exxal 10™ alcohols (i.e., $C_{10}$ alcohols).

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications (including priority documents), test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for producing purified aromatic esters, comprising:
   i) providing one or more feed compound(s) of the following Formulas 1(a) and/or 1(b):

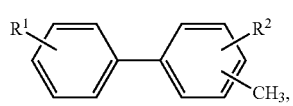

Formula 1(a)

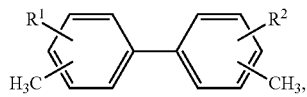

Formula 1(b)

where R1 is a hydrogen or an alkyl and R2 is a hydrogen or an alkyl;

ii) oxidating the feed compound(s) to form a first mixture comprising carboxylic acids and byproduct impurities, the carboxylic acids having the following Formulas 2(a) and/or 2(b):

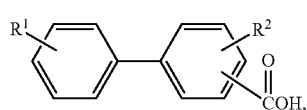

Formula 2(a)

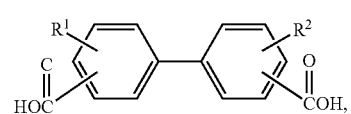

Formula 2(b)

where R1 and R2 are as previously defined and the byproduct impurities comprise aldehydes, acetates, and color body impurities formed from under or over-oxidation of the feed compound(s);

iii) esterifying the carboxylic acids with methyl or ethyl alcohol to form a second mixture comprising at least a portion of the byproduct impurities and methyl or ethyl esters of the following Formulas 3(a) and/or 3(b):

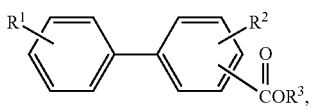

Formula 3(a)

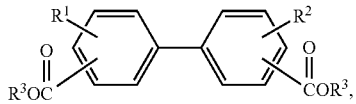

Formula 3(b)

where R1 and R2 are as previously defined and R3 is an alkyl residual of the methyl or ethyl alcohol;

iv) separating the methyl or ethyl esters from substantially all the byproduct impurities in the second mixture to form purified methyl or ethyl esters;

v) transesterifying the purified methyl or ethyl esters with $C_4$ to $C_{14}$ alcohol to form a third mixture comprising methyl or ethyl alcohol and aromatic esters of the following Formulas 4(a) and/or 4(b):

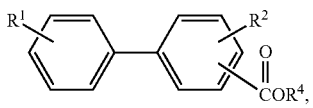

Formula 4(a)

-continued

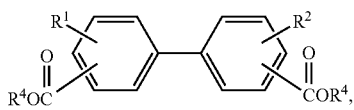

Formula 4(b)

where R1 and R2 are as previously defined and R4 is an alkyl residual of $C_4$ to $C_{14}$ alcohol;

vi) separating the aromatic esters from the methyl or ethyl alcohol in the third product mixture to form a purified aromatic ester product.

2. The method of claim 1, wherein the purified aromatic ester product comprises ≥99.0 wt % aromatic ester based on the weight of the purified aromatic ester product.

3. The method of claim 1, wherein R1 is a methyl group and R2 is hydrogen.

4. The method of claim 1, further comprising cooling the first mixture to form a precipitate, filtering and washing the precipitate with water and/or a solvent to remove at least a portion of byproduct impurities prior to esterifying the carboxylic acid with methyl or ethyl alcohol in step iii).

5. The method of claim 1, wherein the carboxylic acids in step iii) are esterified with methyl alcohol.

6. The method of claim 1, wherein the separation performed in step iv) is by distillation, packed column, and/or vacuum distillation.

7. The method of claim 1, wherein the purified aromatic ester product primarily comprises methyl biphenyl carboxylic acid esters of $C_4$ to $C_{14}$ alcohols.

8. The method of claim 1, wherein the purified aromatic ester product primarily comprises methyl biphenyl carboxylic acid esters of $C_4$ to $C_{14}$ OXO-alcohols.

9. A method for producing purified aromatic esters, comprising:
i) providing a feed comprising dimethylbiphenyl;
ii) oxidating the feed to form a first mixture comprising methyl biphenyl carboxylic acid and byproduct impurities, the byproduct impurities comprising biphenyl dicarboxylic acid, methylbiphenylcarbaldehyde, methylbiphenylmethylacetate, and/or methyl fluorenone;
iii) esterifying the carboxylic acid with methyl or ethyl alcohol to form a second mixture comprising at least a portion of the byproduct impurities and methyl or ethyl esters of methylbiphenylcarboxylic acid;
iv) separating the methyl or ethyl esters of methylbiphenylcarboxylic acid from substantially all the byproduct impurities in the second mixture to form purified methyl or ethyl esters;
v) transesterifying the purified methyl or ethyl esters with $C_4$ to $C_{14}$ alcohol to form a third mixture comprising methyl or ethyl alcohol and methylbiphenyl carboxylic acid esters of the following formula:

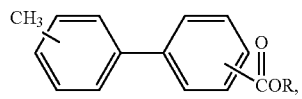

where R is an alkyl residual of $C_4$ to $C_{14}$ alcohol;

vi) separating the methylbiphenyl carboxylic acid esters of $C_4$ to $C_{14}$ alcohol from the methyl or ethyl alcohol in the third mixture to form a purified aromatic ester product.

10. The method of claim 9, wherein the purified aromatic ester product comprises ≥99.0 wt % methylbiphenyl carboxylic acid esters of $C_4$ to $C_{14}$ alcohol based on the weight of the purified aromatic ester product.

11. The method of claim 9, further comprising cooling the first mixture to form a precipitate, filtering and washing the precipitate with water and/or a solvent to remove at least a portion of byproduct impurities prior to esterifying the carboxylic acid with methyl or ethyl alcohol in step iii).

12. The method of claim 9, wherein the carboxylic acids are esterified with methyl alcohol.

13. The method of claim 1, wherein the separation performed in step iv) is by distillation, packed column, and/or vacuum distillation.

14. The method of claim 1, wherein the purified aromatic ester product primarily comprises methyl biphenyl carboxylic acid esters of $C_4$ to $C_{14}$ OXO-alcohols.

* * * * *